US006993390B2

(12) United States Patent
Zappala

(10) Patent No.: US 6,993,390 B2
(45) Date of Patent: Jan. 31, 2006

(54) IMPLANTABLE DEVICE AND METHOD FOR MANAGING ERECTILE DYSFUNCTION

(76) Inventor: Stephen M. Zappala, 98 Rattlesnake Hill Rd., Andover, MA (US) 01810

( * ) Notice: Subject to any disclaimer, the term of this patent is extended or adjusted under 35 U.S.C. 154(b) by 248 days.

(21) Appl. No.: 10/005,390

(22) Filed: Dec. 3, 2001

(65) Prior Publication Data

US 2004/0073268 A1    Apr. 15, 2004

(51) Int. Cl.
*A61N 1/36* (2006.01)
(52) U.S. Cl. .......................................... 607/39
(58) Field of Classification Search ............. 607/1–3, 607/39, 40, 138, 143
See application file for complete search history.

(56) References Cited

U.S. PATENT DOCUMENTS 4,585,005 A * 4/1986 Lue et al. ..................... 607/39
5,454,840 A * 10/1995 Krakovsky et al. ........... 607/39
5,938,584 A *  8/1999 Ardito et al. ................. 600/38
6,169,924 B1 * 1/2001 Meloy et al. .................. 607/39

* cited by examiner

*Primary Examiner*—George R. Evanisko
(74) *Attorney, Agent, or Firm*—Jenifer E. Haeckl; Mirick, O'Connell, DeMallie & Lougee, LLP

(57) ABSTRACT

An implantable device and method for managing a patient's erectile dysfunction, wherein the device generally comprises: at least one power source member that is adapted to be implanted in the patient's lower abdominal wall; at least one pulse generating member that is adapted to be implanted in the patient's lower abdominal wall; and at least one electrode that is adapted to be implanted at the suprapubic level of the patient's neurovascular bundle of the phallus, is connected to said power source member and pulse generating member, and is adapted to electrically stimulate the neurovascular bundle upon selective activation by the patient.

9 Claims, 3 Drawing Sheets

IMPLANTABLE DEVICE AND METHOD FOR MANAGING ERECTILE DYSFUNCTION

FIELD OF THE INVENTION

The invention relates to devices and methods for managing erectile dysfunction and more specifically to a method and implantable device adapted to electrically stimulate the neurovascular bundle (NVB) of the phallus.

BACKGROUND OF THE INVENTION

Erectile dysfunction, which is the persistent inability to attain and maintain penile erection sufficient for intercourse, is a major health issue among males and especially among the AX aging male population. The causes of erectile dysfunction include vasculogenic, neurogenic, endocrinologic and psychogenic. The etiology of erectile dysfunction is heterogeneous, yet, as id noted, is usually associated with vascular disease, endocrinopathy or a neural injury to the central or peripheral nervous system. Management options for erectile dysfunction depend on the cause of the dysfunction and include medical and surgical therapies and vacuum erection devices, each with their own limitations and complications.

Medical therapies include the oral, transcutaneous (penile injection) and transurethral (e.g. MUSE System) routes of delivery of various pharmacologic agents. See, for example, U.S. Pat. No. 5,916,569 to Spencer et al., U.S. Pat. No. 5,925,629 to Place, and U.S. Pat. No. 6,156,753 to Doherty, Jr. et al. However, many men are not suitable candidates for oral agents such as sildenafil (Viagra; Pfizer, New York), a phosphodiesterase inhibitor, because of potential life threatening interactions with cardiac medications such as nitrates.

Penile (intracavernosal) injection therapy with vasodilator agents such as prostaglandin $E_1$, papaverine, nitric oxide, phentolamine, apomorphine, or vasoactive intestinal peptide (VIP) is a well-accepted method. The technique however must be taught to anxious patients with careful attention to the dose, injection sites, and the amount of the agent. Many patients withdraw from intracavernosal injection therapy because of the anxiety associated with self-injection, recurrent cutaneous ecchymoses, painful injections, or associated corporal fibrosis (Peyronie's Disease). Moreover, patients are uncomfortable when they travel through public airports or to foreign countries with syringes and medications. These limitations, associated with the complete loss of spontaneity, are the main reasons for discontinuation in an otherwise successful pharmacologic erection program.

Surgically invasive procedures have been reserved for those men who fail conservative therapies; these options include revascularization procedures, penile prostheses and cavernous nerve stimulation devices, e.g. U.S. Pat. No. 5,938,584 to Ardito et al. and U.S. Pat. No. 6,169,924 B1 to Meloy et al. Penile prostheses are generally last resort because implantation results in irreparable damage to the cavemosal tissue. Agents and devices specifically designed to stimulate the NVB of the phallus have not previously been successful because of the size of the NVB, sensitivity of the NVB to neural fibrosis, and extensive distal, neural damage resulting from surgical procedures such as a radical prostatectomy.

SUMMARY OF THE INVENTION

It is therefore a primary object of this invention to provide an implantable device and method for managing erectile dysfunction that is effective, suitably sized to minimize damage to the NVB, and allows for spontaneity.

It is a further object of this invention to provide an implantable, transvenous neural stimulator that applies a low electrical voltage to the dorsal NVB of the phallus as the primary or adjunctive therapy for erectile dysfunction.

It is a further object of this invention to provide a user with an implantable device and method for managing erectile dysfunction that enables the user to selectively apply a low electrical voltage to the user's NVB.

The preferred embodiment of the implantable device of the invention for managing a patient's erectile dysfunction, generally comprises: at least one power source member that is adapted to be implanted in the patient's lower abdominal wall; at least one pulse generating member that is adapted to be implanted in the patient's lower abdominal wall; and at least one electrode that is adapted to be implanted at the suprapubic level of the patient's neurovascular bundle of the phallus, is connected to said power source member and pulse generating member, and is adapted to electrically stimulate the neurovascular bundle upon selective activation by the patient.

The device may further comprise an elongated lead, to which said electrode is fixed, that connects said electrode to said power source member and pulse generating member; and may further comprise a means for remotely activating said power source member and said pulse generating member, wherein the power source member preferably comprises a high impedance battery and the pulse generating member is adapted to emit low amplitude, high frequency pulses. The lead preferably has an outside diameter of about 2 mm or less, to which the electrode is attached and may comprise at least one extension cable having a length sufficient to connect said electrode to said power source member and said pulse generating member, wherein said power source member and said pulse generating member are adapted to be deactivated automatically when a predetermined electrical potential is reached. The power source member and pulse generating member of the invention are preferably adapted to be deactivated automatically after a predetermined temporal period has passed and are preferably housed together within a titanium shell that is adapted to be implanted in a subcutaneous pocket in the patient's abdominal wall. The pulse generating member is adapted to emit electrical pulses of about 10 to 40 Hz and 1 to 5.5 V and the electrode is preferably provided with a tip that comprises an indifferent material.

Another preferred embodiment of the device of the invention for managing a patient's erectile dysfunction, comprises: at least one power source member and at least one pulse generating member housed in a biocompatible shell that is adapted to be implanted in a pocket of the patient's abdominal wall; and at least one electrode that is provided with an indifferent tip, is adapted to be implanted at the suprapubic level of the patient's neurovascular bundle of the phallus, is connected to said power source member and pulse generator, and is adapted to electrically stimulate the neurovascular bundle upon selective activation by the patient; wherein said pulse generating member is adapted to generate pulses of about 10 to 40 Hz and 1 to 5.5 V when selectively activated by said patient.

The preferred method of the invention, for managing a patient's erectile dysfunction, generally comprises the steps of: providing an implantable delivery device, comprising, at least one power source member that is adapted to be implanted in the patient's lower abdominal wall; at least one pulse generating member that is adapted to be implanted in the patient's lower abdominal wall; and at least one electrode that is adapted to be implanted at the suprapubic level of the patient's neurovascular bundle of the phallus, is connected to said power source member and pulse generator, and is adapted to electrically stimulate the neurovascular bundle upon selective activation by the patient surgically implanting said device so that, at least one of said power source members is implanted in the patient's abdominal wall; at least one of said pulse generating members is implanted in the patient's abdominal wall; at least one of said electrodes is implanted at a suprapubic level of the patient's neurovascular bundle via the dorsal vein of the phallus; activating said power source member to initiate said pulse generator to generate electrical pulses to said electrode and electrically stimulate the patient's neurovascular bundle.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS AND METHODS

The inventive device is an implantable, transvenous neural stimulator that applies a stimulating, low electrical voltage to the NVB of the phallus as the primary or adjunctive therapy of erectile dysfunction. The device is activated by an external signaling source and will deactivate spontaneously after a temporal period or when a predetermined electrical potential is reached. The device is preferably surgically implanted into the hypogastric, internal iliac, pudendal, or the dorsal vein of the phallus with the generator and the battery positioned into a subcutaneous pouch of the lower abdominal wall. A test or simulation procedure can be performed prior to permanent implantation of the device. The device is multiprogrammable from the external source.

Figure 2:
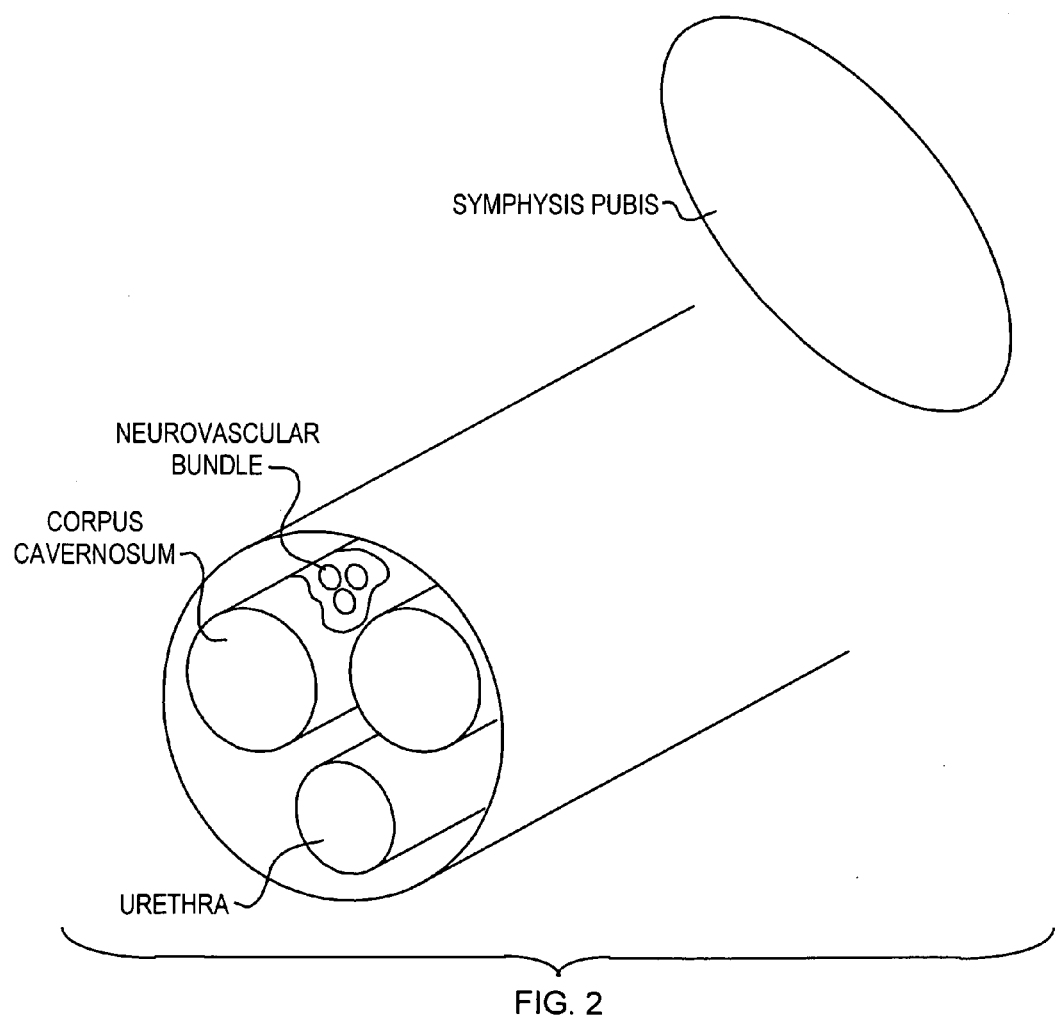
FIG. 2 is a cross-sectional side view of the patient's neurovascular supply of the phallus within which the preferred embodiment shown in FIG. 1 is adapted to be implanted according to the method of the invention.

The neurovascular anatomy of the phallus is relatively constant with the neural tissue routinely identified and located within the intercavemosal space. The NVB contains both neural and vascular structures (arteries, veins) and its course runs parallel to the cavernosal bodies. Both structures are subcutaneous within the phallus (FIG. 2) and proximally diverge at the level of the membranous urethra. The dorsal vein is located anterior to the membranous urethra while the neural bundles diverge over the dorsolateral aspect of the prostate. NVB stimulation is A, associated with relaxation of the corpus cavemosal smooth muscle, tunica albuginea, and vascular dilation via the release of vasoactive transmitters such as vasoactive intestinal peptide and nitric oxide.

Figure 1:
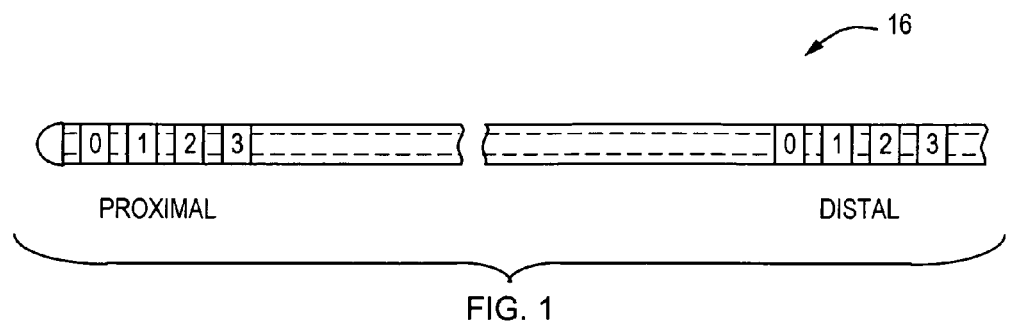
FIG. 1 is a side view of the electrical leads of the preferred embodiment of the device of the invention.
Figure 4:
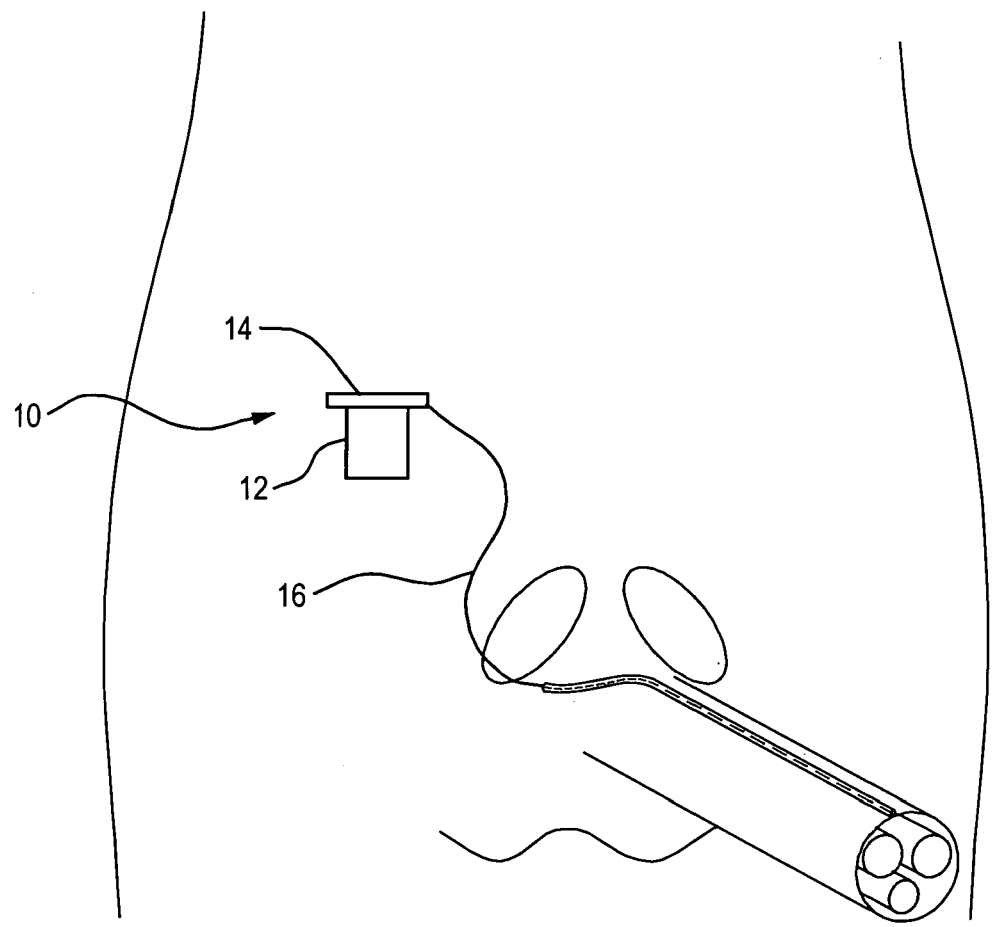
FIG. 4 is a perspective view of an embodiment of the device of the invention implanted in a surgical position.

The dorsal vein neuromodulator (DVN) of the invention, generally shown and referred to in FIG. 4 as device 10, is a surgically implanted device which generally comprises three primary components: high impedance battery/power source 12, pulse generator 14 (low amplitude, high frequency), and lead 16 which preferably comprises at least four electrodes and extension cables. Device 10 is preferably single use and latex free. Lead 16 is preferably a small calibre lead with an outside diameter of about 2 mm or less. Optimal lead placement to the phallic NVB via the dorsal vein is critical to the operation and success of the device. An example of lead 16 is shown in FIG. 1. The battery and pulse generator are housed together in a biocompatible material and further encapsulated within a thin-wall titanium shell that is surgically implanted in its entirety within a subcutaneous pocket in the lower abdominal wall. The leads, which may be unipolar and/or bipolar, are connected and coated with an insulating material such as silicone or polyurethane. The indifferent "pacemaker" tips of the electrodes are preferably stainless steel NP35.

Figure 3A:
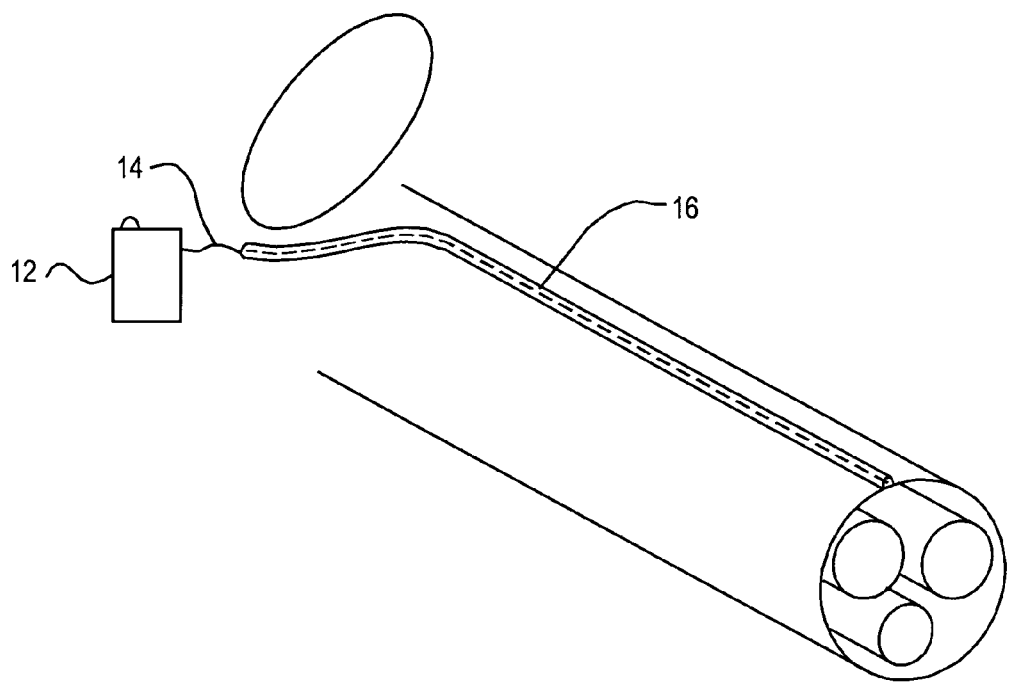
FIG. 3 is a perspective view of an embodiment of the device of the invention in a percutaneous position.
Figure 3B:
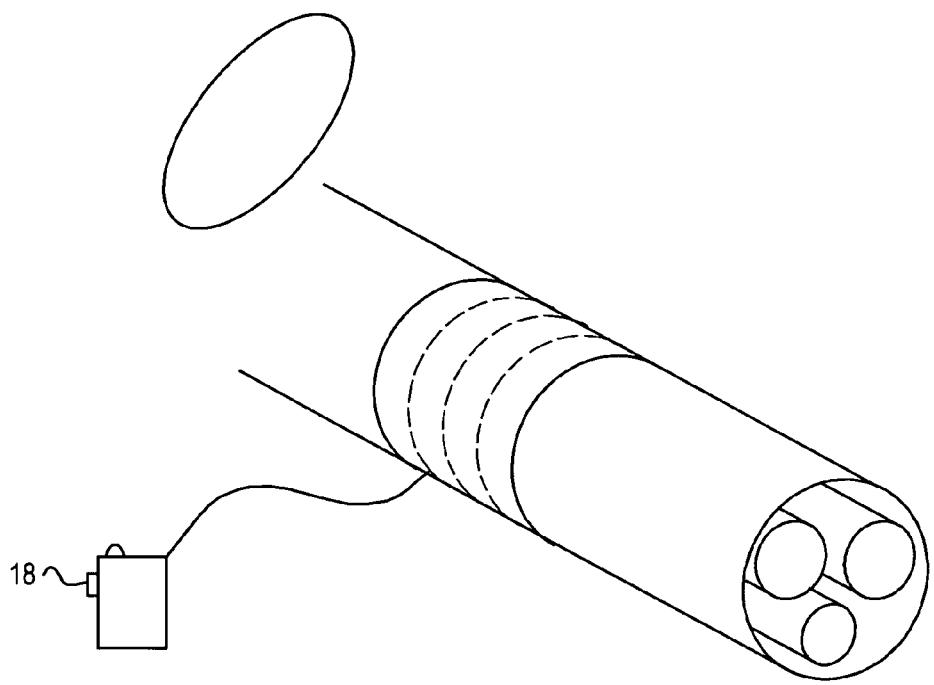

Before permanently implanting the device in a patient, a simulation should be performed to verify the device's potential effectiveness for that particular patient. The primary site for simulation is either transcutaneous (external, prior to radical retropubic or pelvic surgery) or percutaneous via subcutaneous venous collaterals, as shown in FIGS. 3A and 3B, respectively.

The permanent device is implanted at the suprapubic level of the dorsal vein as the vein traverses the rectus abdominis fascia The vein is cannulated with an insertion sheath and the stylet is removed. The electrode is inserted through the sheath with fluoroscopic guidance to the periphery of the NVB. Electrode activation is performed intraoperative to guarantee the optimal lead position for transvenous stimulation. The electrode is attached to an extension cable that is connected to the battery/generator. The battery and generator are implanted into a subcutaneous pouch of the lower abdominal wall. The device is connected to an external source during the stimulation to the permanently implanted device.

The patient may selectively regulate the amplitude and rate of stimuli (pulse width) of the stimulation through the external or remote source that utilizes a suitable means 18 for communication such as IR and/or RF transmission. The impedance of the tissue is about 800 to 2000 ohms. To stimulate both the striated and smooth muscle fibers of the phallus, the frequency range of the device should be about 10 to 40 Hz and the stimulating voltage should be programmable from about 1 V to 5.5 V.

The preferred method of the invention for managing erectile dysfunction begins with the step of providing the implantable delivery device of the invention, generally comprising: at least one power source member that is adapted to be implanted in the patient's lower abdominal wall; at least one pulse generating member that is adapted to be implanted in the patient's lower abdominal wall; and at least one electrode that is adapted to be implanted at the suprapubic level of the patient's neurovascular bundle of the phallus, is connected to said power source member and pulse generator, and is adapted to electrically stimulate the neurovascular bundle upon selective activation by the patient surgically implanting said device so that, at least one of said power source members is implanted in the patient's abdominal wall; at least one of said pulse generating members is implanted in the patient's abdominal wall; at least one of said electrodes is implanted at a suprapubic level of the patient's neurovascular bundle via the dorsal vein of the phallus; activating said power source member to initiate said pulse generator to generate electrical pulses to said electrode and electically stimulate the patient's neurovascular bundle.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A device for managing a patient's erectile dysfunction, comprising,
    at least one power source member that is adapted to be implanted in the patient's lower abdominal wall;
    at least one pulse generating member that is adapted to be implanted in the patient's lower abdominal wall;
    at least one electrode that is adapted to be implanted at the suprapubic level of the patient's neurovascular bundle of the phallus, is connected to said power source member and pulse generator, and is adapted to electrically stimulate the neurovascular bundle; and
    a means for enabling the patient to selectively activate said electrode;
    wherein said power source member and said pulse generating member are adapted to be deactivated automatically after a predetermined temporal period has passed.

2. The device of claim 1, further comprising an elongated lead, to which said electrode is fixed, that connects said electrode to said power source member and pulse generating member.

3. The device of claim 1, further comprising a means for remotely activating said power source member and said pulse generating member.

4. The device of claim 1, wherein said pulse generating member is adapted to emit pulses of about 10 to 40 Hz and 1 to 5.5 V, and wherein said power source member comprises a battery.

5. The device of claim 1, wherein said pulse generating member is adapted to emit low amplitude, high frequency pulses.

6. The device of claim 1, further comprising a lead with an outside diameter of about 2 mm or less, to which said electrode is attached and comprises at least one extension cable having a length sufficient to connect said electrode to said power source member and said pulse generating member.

7. The device of claim 1, further comprising a titanium shell, wherein said power source member and said pulse generating member are housed together within said titanium shell that is adapted to be implanted in a subcutaneous pocket in the patient's abdominal wall.

8. The device of claim 1, wherein said pulse generating member is adapted to emit electrical pulses of about 10 to 40 Hz and 1 to 5.5 V.

9. The device of claim 1, wherein said electrode is provided with a tip that comprises an indifferent material.

* * * * *